United States Patent [19]

Liu et al.

[11] Patent Number: 5,643,794
[45] Date of Patent: Jul. 1, 1997

[54] APPARATUS FOR BIOPROCESSING A CIRCULATING FLUID

[75] Inventors: Lee-Cheng Liu, Columbia, Md.; Timothy J. Perlman, Arlington, Mass.; Catherine A. Doyle, Massapequa, N.Y.

[73] Assignee: W.R. Grace & Co.-Conn., Columbia, Md.

[21] Appl. No.: 475,629

[22] Filed: Jun. 7, 1995

[51] Int. Cl.[6] ................................................ C12M 3/00
[52] U.S. Cl. .................. 435/289.1; 435/284.1; 435/309.1; 604/5
[58] Field of Search .................. 435/1.2, 284.1, 435/286.5, 289.1, 297.1, 297.4, 297.2, 299.1, 303.1, 309.1, 309.2, 308.1; 422/44–48; 210/645–647, 782, 521; 604/4–6, 408, 410, 757, 758, 262, 403; 141/114; 222/92, 95, 103, 209, 401, 394; 137/546, 574, 571, 593, 568, 777

[56] References Cited

U.S. PATENT DOCUMENTS

| | | | |
|---|---|---|---|
| 663,712 | 12/1900 | Alexander | 222/401 |
| 1,442,785 | 1/1923 | Scheminger | 137/568 |
| 2,618,409 | 11/1952 | Eisenberger et al. | 222/95 |
| 2,930,393 | 3/1960 | Starling | 137/574 |
| 4,209,392 | 6/1980 | Wallace | 210/23 F |
| 4,223,672 | 9/1980 | Terman et al. | 210/782 |
| 4,383,622 | 5/1983 | Guth | 222/401 |
| 4,540,399 | 9/1985 | Litzie et al. | 604/4 |
| 4,976,707 | 12/1990 | Bodicky et al. | 604/4 |
| 5,014,737 | 5/1991 | Berman | 137/574 |
| 5,053,011 | 10/1991 | Strobel et al. | 222/95 |
| 5,270,192 | 12/1993 | Li et al. | 435/174 |
| 5,328,461 | 7/1994 | Utterberg | 604/4 |
| 5,368,555 | 11/1994 | Sussman et al. | 604/4 |
| 5,503,801 | 4/1996 | Brugger | 604/4 |

OTHER PUBLICATIONS

Marc E. DeBroe et al., "Clinical Experience with Prolonged Combined Hemoperfusion-Hemodialysis Treatment of Severe Poisoning", *Artificial Organs*, Feb. 1981, vol. 5, No. 1, pp. 59–66.

Stella Jones Fitzgibbons, "Making Artificial Organs Work", *Technology Review*, Aug./Sep. 1994, pp. 34–40.

Jacek Rozga et al., "Development of a Bioartificial Liver: Properties and Function of a Hollow-fiber Module Inoculated with Liver Cells", *Hepatology*, vol. 17, No. 2, Feb. 1993, pp. 258–265.

Jacek Rozga et al., "A Bioartificial Liver to Treat Severe Acute Liver Failure", *Annals of Surgery*, vol. 219, No. 5, May 1994, pp. 538–546.

*Primary Examiner*—William H. Beisner
*Attorney, Agent, or Firm*—Fish & Richardson P.C.

[57] ABSTRACT

The invention relates to the safe and effective biotreatment of circulating fluids. In one general aspect of the invention, an apparatus (e.g., liver assist system) for circulating and bioprocessing a fluid (e.g., plasma) includes a conduit for circulating the fluid, an oxygenator for supplying oxygen to the fluid, a pump adapted to circulate the fluid through the conduit, a bioreactor unit, connected within the conduit, adapted to process the fluid, and a container connected within the conduit for receiving and releasing a portion of the fluid.

21 Claims, 3 Drawing Sheets

APPARATUS FOR BIOPROCESSING A CIRCULATING FLUID

BACKGROUND OF THE INVENTION

There is a need for apparatuses which safely and effectively bioprocess a circulating a body fluid, such as whole blood or plasma. As an example, the development of liver support apparatuses has progressed from passive or removal systems to bioactive or biochemical systems. The passive systems have included hemodialysis, hemoperfusion, plasma exchanges, etc. for removing the blood toxins which accumulate during liver failure.

The successful reports of orthotopic liver transplantation in prolonging life has led to the conceptual development of biochemical or cell based liver support systems. These systems consist mainly of bioreactors containing cells. For example, a bioartificial liver device may include a hollow fiber cartridge containing primary pig liver cells. The liver cells are seeded in the extra-capillary space of the hollow fibers, and blood or plasma is perfused through the lumen of the fibers. Microporous hollow fibers permit passage of plasma proteins but prevent the passage of cells (e.g., blood cells and liver cells), thereby allowing the transport of soluble and protein-bound substances from the plasma across the hollow fiber walls and into the space occupied by the porcine hepatocytes.

SUMMARY OF THE INVENTION

This present invention relates to bio-treatment of circulating fluids. A general aspect of the invention involves an apparatus (e.g., liver assist system) for circulating and bioprocessing a fluid (e.g., plasma or lymph fluid) which includes a conduit for circulating the fluid, an oxygenator connected within the conduit for supplying oxygen to the fluid, a pump adapted to circulate the fluid through the conduit, a bioreactor unit connected within the conduit for processing the fluid, and a container also connected within the conduit for receiving and releasing a portion of the fluid. If desired, a charcoal filter can also be added to the apparatus of this invention for pre-filtering the fluid before it is bio-treated in the bioreactor unit.

The apparatus may include an in-port for receiving fluid from an external system (e.g., a plasma separation machine or a patient) and an out-port for returning the fluid to the external system. When used in such a manner, the apparatus is said to be operated as an open system. In this on-line arrangement, it is generally preferred that the fluid be received and treated by the bioreactor unit prior to being received at the container in order to avoid unnecessary dilution of the fresh fluid. In an open-system operation, it is preferred that the apparatus include bypass structure, which upon actuation, prevents flow of the fluid between the conduit and the external system. The bypass structure allows the apparatus to be isolated from the external system in the event of an emergency or to be simply detached and allowed to operate independently.

Alternatively, the apparatus may be used independently as a closed system. In a closed operation, the container itself may serve as the source of the fluid to be treated by the apparatus, or a separate container may be attached to the in-port of the apparatus to supply an untreated fluid.

The apparatus may include a heater for maintaining the fluid within a temperature range or may be placed in a temperature-controlled environment (e.g., heated room) which maintains the temperature of the fluid. Preferably, the oxygenator and heater are provided as an integral unit.

In an embodiment of the apparatus, the container includes a first compartment configured to receive the fluid into the container through an inlet disposed in the first compartment, and a second compartment configured to receive fluid overflowing from the first compartment and to allow flow of the fluid out of the container through an outlet disposed in the second compartment. The container is multifunctional. The inlet and outlet are configured within the compartments to provide a reservoir to serve as a buffer to compensate for fluctuations in the flow rate of the fluid (i.e., surges). The container is preferably sized to have a sufficient cross-sectional area with respect to the cross-sectional area of the conduit to reduce the velocity of the fluid entering the container. Moreover, the container, when made of a transparent material, provides a window for monitoring, either visually or electronically, the volume of the fluid within the apparatus. The flow rate of the fluid entering the apparatus can then be adjusted based on volume changes, if necessary. Further, the inlet and outlet can be positioned with respect to each other so that particulate matter (e.g., fibrins)—which can cause clogging within the conduit and the components disposed therein (i.e., oxygenator, filters, bioreactor)—are substantially prevented from being released from the container. In addition, the compartments may be physically separated by a dividing element with the particulate matter trapped within the compartment associated with the inlet. The container may include additional compartments between the compartments associated with the inlet and outlet. In this arrangement, the fluid successively overflows from one compartment to the next until reaching the outlet.

The container may include a vent to allow the escape of gas in the form of bubbles. Bubbles which collect within the oxygenator, charcoal filter and bioreactor unit of the apparatus can reduce the effectiveness of these components in performing their respective functions.

The apparatus may be used in conjunction with a cell inoculation device connected to a second in-port of the apparatus. The cell inoculation device inoculates (or seeds) cells into the bioreactor unit of the apparatus. The cell inoculation system includes: a receptacle with an entrance for receiving cells into an interior volume of the receptacle, a tube extending from an exit of the receptacle configured to allow the withdrawal of the cells from the interior volume, and a pressure mechanism, attached to the receptacle, for providing a positive pressure within the interior volume of the receptacle with respect to the external atmosphere of the receptacle. The positive pressure within the interior volume of the receptacle induces the withdrawal of the cells from the receptacle into the bioreactor unit. The receptacle may include a second inlet configured to introduce a rinsing solution to the interior volume of the receptacle. The pressure mechanism may include a pressure cuff adapted to squeeze a receptacle made of a flexible material. Alternatively, the pressure mechanism may include a source for providing pressurized gas to the interior volume of the receptacle.

Other features and advantages of the invention will become apparent from the following drawings and detailed description, and also from the claims.

DESCRIPTION OF THE PREFERRED EMBODIMENTS

Figure 1:
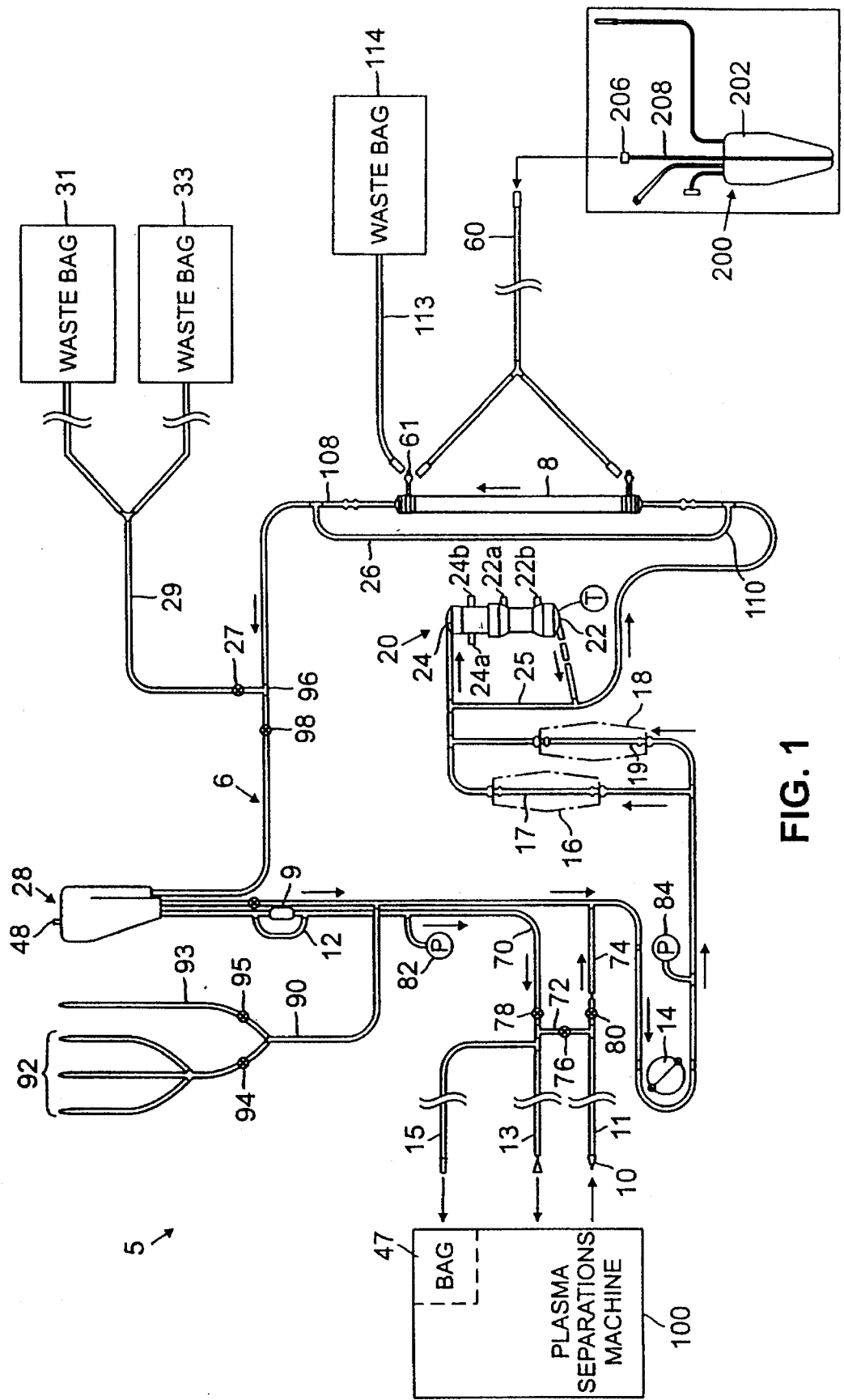
FIG. 1 is a schematic representation of a liver assist system according to the invention.

Referring to FIG. 1, a schematic representation of a liver assist system 5 includes a conduit 6 made of disposable plastic tubing (e.g., PVC) for circulating plasma through a bioartificial liver (BAL) device 8 which contains liver cells. Conduit 6 may include sections of tubing (11, 13, 70, 74) used to connect liver assist system 5 to an external system, such as a plasma separation machine 100. Connected within conduit 6, in a series arrangement, are a peristaltic pump 14, optional charcoal filters 16, 18, an oxygenator/heat exchange unit 20, the BAL device 8, and a reservoir bag 28, each of which will be discussed in greater detail below. Liver assist system 5, in use, supports approximately 650 ml of fluid with about 120 ml disposed within conduit 6.

Prior to introducing the plasma to liver assist system 5, saline (or other suitable fluid) is used to entirely fill conduit 6 as well as the components of the system. Reservoir bag 28 is also filled sufficiently to provide a buffer for incoming fluid and indicates when liver assist system is entirely filled and primed. This process is part of a cleansing process in which the system is rinsed and primed using a method described below.

In general, plasma is provided to the liver assist system 5 at an in-port 10 via tubing 11 and is pumped through the system using pump 14 in the direction indicated by arrows. Filters 16, 18 prefilter the plasma of toxins while oxygenator/heat exchange unit 20 oxygenates and maintains the temperature of the plasma within a predetermined temperature range. The plasma is then received by the BAL device 8 that has been seeded with liver cells which remove toxins from the plasma. The reservoir bag 28 receives the treated plasma before being recirculated back through the system.

Liver assist system 5 is generally used in conjunction with a cell inoculation device 200 (described below) which provides liver cells to the BAL device. The liver cells remove or modify toxic substances from the plasma.

In FIG. 1, liver assist system 5 is shown as part of an on-line system that is connected to an external system (e.g., plasma separation machine 100) which supplies plasma to the liver assist system for treatment. The plasma from plasma separation machine 100 is provided to conduit 6 from tubing 11 and returned from liver assist system 5 via tubing 13.

The plasma separation machine 100 shown in FIG. 1 separates plasma to be treated from whole blood of a human patient. In other on-line applications, the external system may be a patient and the whole blood of the patient is circulated and bioprocessed in liver assist system 5. It is also important to note that liver assist system 5 may be used in an off-line operation in which a source of plasma to be treated is provided, for example, in a bag and connected to an in-port 10 of the liver assist system 5. In this case, the untreated plasma is allowed to circulate through the liver assist system to be detoxified and then dispensed at an out-port of the system.

Disposed within the conduit 6 is pump 14, which provide sufficient drive to force the plasma from tubing 11 to flow through the conduit 6 in the direction indicated by arrows. The plasma flows at a user selectable flow rate between 50 and 1000 ml/min, nominally 400 ml/min. The system optionally includes a pair of charcoal filters 16, 18 for pre-filtering the plasma before it is provided to the BAL device 8. Only one of the filters is in use at any given time, the other being available to allow continued use of the system when one of the filters needs to be replaced. Clamps (not shown) are used to allow and/or restrict flow through one or the other of the filters. Either of the charcoal filters 16 or 18 may be replaced with a length of tube 17 or 19 to provide a bypass path around the charcoal filter when system 5 is in use.

Plasma from the filters passes to oxygenator/heat exchange unit 20 having an oxygenator 22 which supplies oxygen to the plasma and a heater 24. Oxygenator 22 receives, at inlet 22a, pressurized sterile gas (e.g., 30% $O_2$, 5% $CO_2$, 65% $N_2$) from an external gas source (not shown). The plasma passes through semi-permeable hollow fibers disposed within the oxygenator 22 to collect oxygen needed by the liver cells inoculated within BAL device 8. An optional oxygen measurement system may be used to measure the difference between the oxygen content of the plasma entering and exiting BAL device 8 to provide an indication of the effectiveness of the BAL device. The pressurized gas provided to the oxygenator passes through hydrophobic membranes disposed respectively at inlet 22a and outlet 22b.

Plasma flowing through heater 24 is maintained at a predetermined temperature (e.g., 37° C.) by heat conduction as it flows past a heat exchanger within the oxygenator. Heated water from an external water heater/recirculator (not shown) is received at inlet 24a of the heater and returned via outlet 24b for reheating. A bypass line 25 with a clamp (not shown) is provided to bypass oxygenator/heat exchange unit 20 and through the system to allow the cleaning or replacement of the oxygenator/heat exchange unit 20.

Plasma from oxygenator/heat exchange unit 20 is received by the bioartificial liver device 8 (e.g., a replaceable hollow fiber cartridge inoculated with cells). BAL device 8 includes a bundle of hollow fibers. In one embodiment, the fibers are inoculated with liver cells so that toxic substances within the plasma are removed as the plasma passes between the fibers. Alternatively, the plasma can pass along the axial length of the fibers with the liver cells introduced between the fibers. A bypass line 26 having a manual clamp is provided to bypass the BAL device 8, for example, when the BAL device requires replacement, maintenance, or cleansing (described below). During operation of liver assist system 5, tubing 29 attached to waste bags 31, 33 (described below), is closed off from flow of plasma with pinch valve 27.

Figure 2:
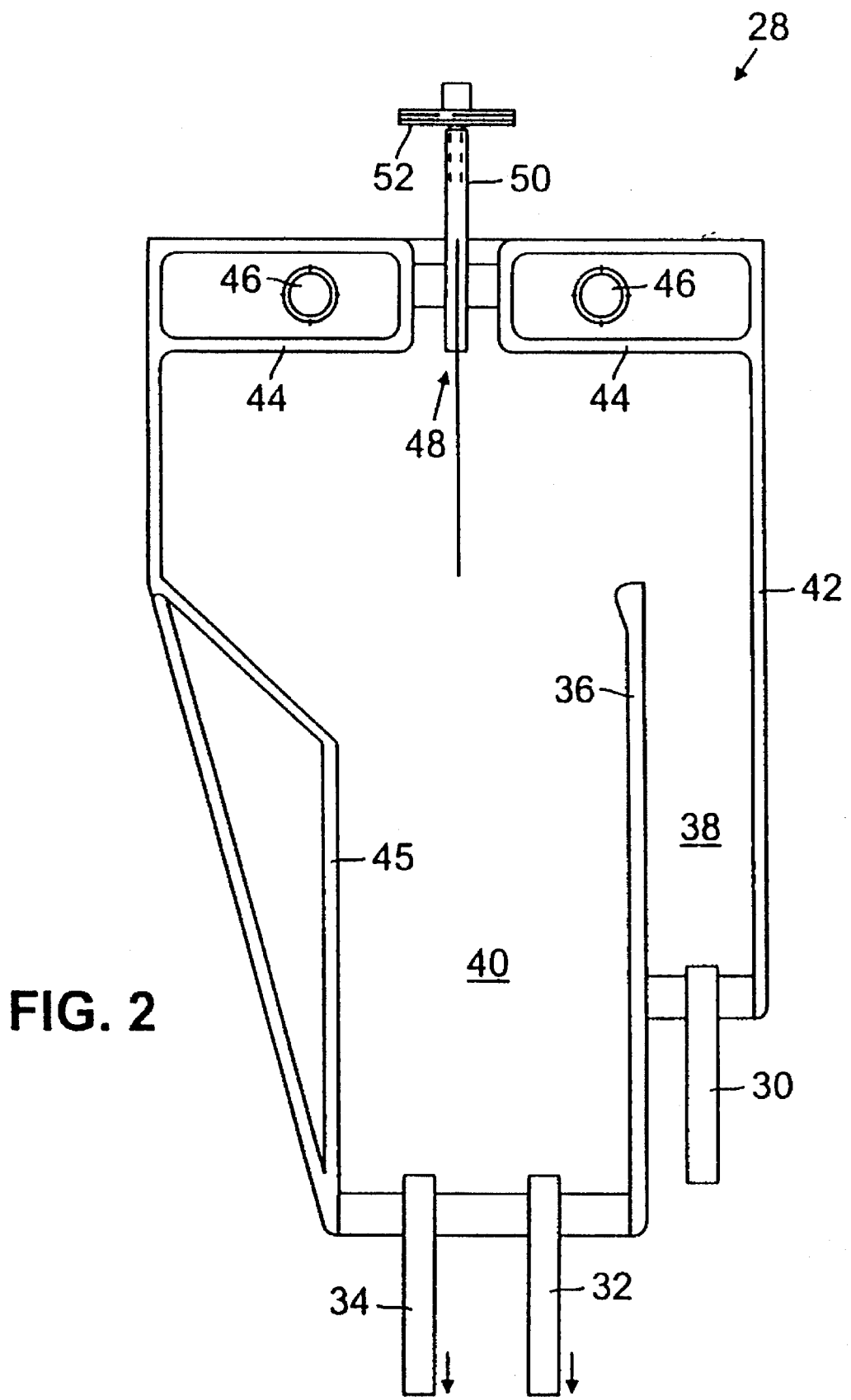
FIG. 2 is a plan view of a container adapted to receive and release the processed fluid treated within the liver assist system of FIG. 1.

The treated plasma is then conveyed to the plasma reservoir bag 28 before being recirculated through the system with a portion also being returned to the plasma separation machine 100. Referring to FIG. 2, reservoir bag 28 is made of a strong and pliable material, such as PVC plastic. Reservoir bag 28 includes an inlet 30 and a pair of outlets 32, 34 at the lower end of the bag. Outlet 32 provides fluid back to BAL device 8 for further treatment, while outlet 34 leads to the plasma separation machine 100. A dividing partition 36 between inlet 30 and outlets 32, 34 define a pair of compartments 38, 40. Compartment 38 provides an inlet channel and compartment 40 provides an overflow reservoir for holding a volume (e.g., 100 ml) of fluid. Dividing partition 36 between compartments 38, 40 ensures that particulate matter which may be in the plasma is trapped in compartment 38 and prevented from returning to the liver assist system 5 where it may cause clogging of conduit 6 and the components of the system. Due to the increased cross-sectional area of compartment 38 (with respect to the cross-sectional area of inlet 30), the velocity of the plasma entering reservoir bag 28 decreases. Thus, the particulate matter is allowed to settle in the lower portion of compartment 38. The plasma overflowing into compartment 40 is temporarily held before being recirculated to the liver assist system 5 or plasma separation system 100. Reservoir bag 28 also serves to accommodate surging of the plasma.

Reservoir bag 28 may include multiple compartments between inlet 30 and outlets 32, 34 so that the particulate matter will settle in the bottom portions of each compartment as the plasma overflows from one compartment to the next.

A vent 48 is provided at the top of reservoir bag 28 by a tube 50 which extends to a filter 52 (e.g., 0.2 micron). Vent 48 allows gas within the plasma, in the form of bubbles, to escape.

One approach for forming reservoir bag 28 is to overlay two sheets of PVC plastic cut in the shape of the bag. RF energy is then applied to the periphery of the sheets to provide an air-tight edge 42 to the bag. Support seams 44, along the top portion of bag 28, are provided where holes are punched for allowing the bag to be hung from a support. An additional support seam 45 at the side of the bag is provided along one side of bag 28 so that compartment 40 defines a reservoir of sufficient depth. Support seams 44 and 45, as well as dividing partition 36, are formed also using the RF heat-sealing technique.

The level of plasma in reservoir bag 28 can be visually observed by the operator of the system who can manually release or restrict flow of the plasma from the bag to maintain a proper level of plasma in the bag, for example, using line 15. The level can also be maintained using an electronic device which controls pump 14 of the liver assist system and/or a pump of the plasma separation machine 100.

An optional filter 9 with a bypass 12 may be included within tubing 70 for filtering particulate matter from the plasma returning to the external system. Filter 9 serves to capture and prevent the circulation of cells released into conduit 6 in the event of a catastrophic failure of the hollow fibers in BAL device 8. Bypass 12 provides a flow path for the plasma if filter 9 becomes clogged or needs replacement.

Liver assist system 5 can also be used in a closed, off-line system operation, with reservoir bag 28 serving as the source of the plasma being introduced to the system. In this case, reservoir bag will generally be larger in size, for example, 2 liters.

Figure 3:
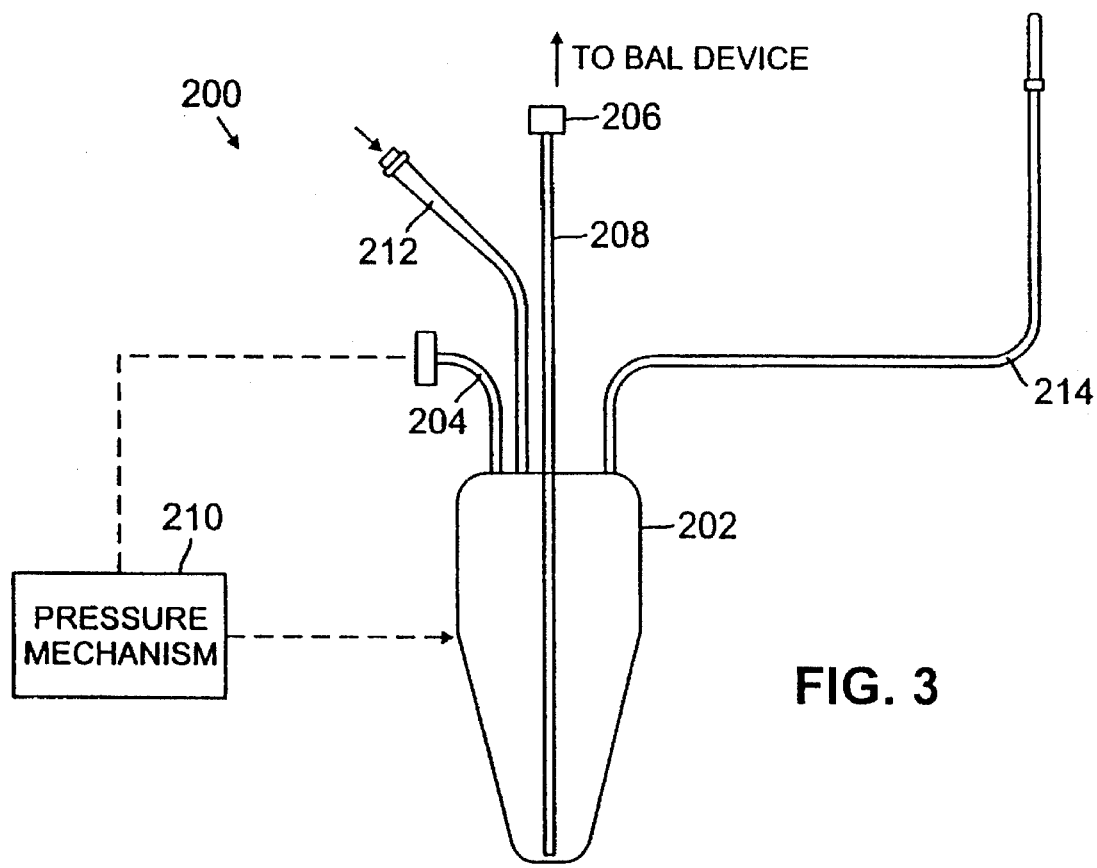
FIG. 3 is a diagrammatic view of a cell inoculation device for inoculating cells into the bioreactor unit of the liver assist system of FIG. 1.

Referring to the lower right inset of FIG. 1 and FIG. 3, a cell inoculation device 200 includes a flexible seeding bag 202 formed of plastic (e.g. PVC) in which harvested liver cells to be inoculated in the BAL device 8 are held. Cell inoculation device 200 includes an inlet 212 through which cell suspension is dispensed within seeding bag 202 and an outlet 206 which can be connected, for example, to an inlet tube 60 of the liver assist system 5 (FIG. 1). Outlet 206 is connected to a tube 208 which extends to the bottom portion of seeding bag 202 to maximize the removal of cell suspension. The seeding bag 202 is easily attached/detached from liver assist system 5 and is also a convenient receptacle for transporting the cells.

The liver cells are removed from seeding bag 202 into BAL device 8 using a pressure mechanism device 210 attached to cell inoculation device 200. In one embodiment, pressure mechanism device 210 may be a pressure cuff which is wrapped around seeding bag 202. Upon manual or automatic actuation, positive pressure is provided within the bag causing the cells to rise through tube 208 and out of outlet 206. In another embodiment, a pressurized gas source may be used to provide positive pressure via inlet hose 204 to the inside of the bag causing the cells to rise through tube 208. In still a further embodiment, the cells can be extracted from the bag by attaching a pump to outlet 206 of tube 208 to pump the cells out of the bag.

A rinsing tube 214 is provided at the top of bag 202 for introducing a rinsing solution (e.g., saline) to ensure the removal of residual cells that may settle within the bottom of bag.

Referring again to FIG. 1, liver assist system 5 includes bypass conduits which allow flexibility of use and ensure safety in case of emergency. For example, the connection between the liver assist system 5 and the plasma separation system 100 (or other external system) includes tubing 70 which provides a path of flow for a portion of the treated plasma back to plasma separation machine 100 from outlet 34 of reservoir bag 28. A bridge section 72 connects tubing 70 to tubing 74 which introduces the plasma to be treated to BAL device 8. When the plasma separation machine 100 is being used on-line with liver assist system 5, a pinch valve 76 is closed to prevent flow of plasma through bridge section 72 so that all of the plasma returning along tubing 70 flows to plasma separation machine 100. In the event of an emergency, when it becomes necessary to prevent interflow between the systems, pinch valves 78, 80 are closed and pinch valve 76 is opened. In this arrangement, plasma from the plasma separation machine 100 can be made to flow through line 11, through open pinch valve 76, back to plasma separation machine 100 through line 13. Line 15 may be open to a plasma storage bag 47 within machine 100. Bag 47 may act as a compliant chamber to account for variations of the flow rate in and out of plasma separation machine 100 through bypass 72. Pressure transducers 82, 84 are provided within conduit 6 to sense extreme or inadequate levels of pressure. In these situations, signals from transducers 82, 84 are used to control pinch valves 76, 78, 80 and pump 14, and may also be used to provide a visual or audible warning signal to alert the operator of the condition. Sampling ports may also be provided along conduit 6 to examine the characteristics of the plasma.

The liver assist system 5 provides the following features for rinsing and priming conduit 6 and its components (i.e., oxygenator, filters, and bioreactor unit). Tubing 92, 93, operating in conjunction with pinch valves 94, 95, allows the introduction of two separate solutions for priming and rinsing conduit 6 and the components disposed therein. One solution (e.g., saline) is introduced through tubing 92 with the other solution (e.g., 5% dextrose) introduced through tubing 93. Bypass segments allow for flushing the components independently or in series. The components may be rinsed and primed in any order.

Tubing 92, 93 for introducing priming solution and tubing 29, 113 leading to integral waste bags 31, 33, 114 create a closed system and provide an aseptic method of rinsing and priming the liver assist system 5. In a preferred configuration, tubing 29, 92, 93 may be sealed and removed to condense the liver assist system once it is ready to receive plasma. The use of pinch valves 27 and 98 allows the priming solution to be directed to waste bags 31, 33 after one pass before flowing to the waste bags or recirculated through the liver assist system 5. The hollow fiber cartridge of the BAL device (without inoculated cells) is rinsed and primed along the fibers with the waste solution directed to waste bags 31, 33. A separate waste bag 114 is connected to BAL device 8 at in-port 61. The extra-capillary space between the bundle of fibers is primed, and pores of the fibers are rinsed, with the waste solution directed to waste bag 114. When cleansing of BAL device 8 is complete, BAL device 8 is completely filled with saline and ready to receive cells.

Tubing 70, 74 between liver assist system 5 and the plasma separation machine 100 is rinsed by opening valves 78, 80 for a period of time to allow some of the saline to flow through the tubing. It is generally important that the liver assist system 5 be fully primed with the priming solution at the initiation of plasma processing.

Liver cells from cell inoculation device 200 are then introduced at inlet 60 of BAL device 8 and the saline within the extra capillary space of the BAL device is displaced into waste bag 31, 33. Waste bags 31, 33, and 114 and lines 60 and 113 are then removed. In this condition, liver assist system 5 is considered to be primed and ready to receive plasma.

Other Embodiments

From the above description, one skilled in the art can easily ascertain the essential characteristics of the present invention, and without departing from the spirit and scope thereof, can make various changes and modifications of the invention to adapt it to various usages and conditions. For example, liver assist system 5, described above for use as an artificial liver, may be used in other medical applications. Moreover, the concept may be applicable to industrial operations. Thus, other embodiments are also within the claims.

What is claimed is:

1. An apparatus for circulating and bioprocessing a fluid, comprising:
   a conduit for circulating the fluid;
   an oxygenator, connected within said conduit, adapted to supply oxygen to the fluid;
   a pump adapted to circulate the fluid through the conduit;
   a bioreactor unit, connected within said conduit, adapted to process the fluid; and
   a container, connected within said conduit, including:
      a first compartment configured to receive the fluid into said container;
      an inlet connected at a bottom end of said first compartment to provide the fluid into said first compartment, the cross-sectional area of the first compartment abruptly increasing from that of the cross-sectional area of the inlet; and
      a second compartment configured to receive fluid overflowing from said first compartment; and
      an outlet connected to said second compartment to allow flow of the fluid out of said second container.

2. The apparatus of claim 1 further comprising an in-port connected within the conduit and configured to receive the fluid from an external system, and an out-port connected within the conduit and configured to return a portion of the processed fluid to the external system.

3. The apparatus of claim 2 further comprising bypass structure which upon actuation prevents flow of the fluid between said conduit and the external system.

4. The apparatus of claim 2 wherein the external system is a plasma separation apparatus.

5. The apparatus of claim 4 further comprising bypass structure which upon actuation prevents flow of the fluid between said conduit and the external system.

6. The apparatus of claim 5 wherein the fluid from said in-port circulates through said bioreactor unit prior to being received by said container.

7. The apparatus of claim 6 wherein said container includes a vent to allow the escape of gas.

8. The apparatus of claim 7 wherein said oxygenator is integrally connected to a heater adapted to maintain the fluid within a temperature range.

9. The apparatus of claim 8 further comprising a filter, connected within said conduit, for filtering the fluid, wherein the fluid from said in-port circulates through said filter prior to being received by said oxygenator and then by said bioreactor unit.

10. The apparatus of claim 2 wherein unprocessed fluid from said in-port circulates through said bioreactor unit prior to being received by said container.

11. The apparatus of claim 10 wherein said container includes a vent to allow the escape of gas.

12. The apparatus of claim 1 wherein said oxygenator is integrally connected to a heater adapted to maintain the fluid within a temperature range.

13. The apparatus of claim 1 further comprising a second in-port and a cell inoculation device for inoculating cells into said bioreactor unit, said inoculation device connected to said second in-port and having:
   a receptacle with an interior volume and an entrance for receiving cells into said interior volume;
   a pressure mechanism, attached to said receptacle, for providing a positive pressure within the interior volume of said receptacle with respect to the external atmosphere of said receptacle to induce the withdrawal of the cells from said receptacle; and
   a tube extending from an exit of said receptacle configured to allow the withdrawal of the cells from the interior volume.

14. The apparatus of claim 1 wherein said container includes a vent to allow the escape of gas.

15. The apparatus of claim 1 further comprising a bypass conduit extending around the bioreactor unit.

16. An apparatus for receiving a fluid from a plasma separation apparatus, circulating and bio-processing the fluid, and returning a portion of the fluid to the plasma separation apparatus, said apparatus comprising:
   a conduit for circulating the fluid;
   an in-port connected within said conduit and configured to receive the fluid from the plasma separation apparatus and an out-port configured to return a portion of the processed fluid to the plasma separation apparatus;
   an oxygenator, connected within said conduit, adapted to supply oxygen to the fluid;
   a pump adapted to circulate the fluid through said conduit;
   a bioreactor unit, connected within said conduit, adapted to and process the fluid;
   a container connected within said conduit adapted to receive the processed fluid from said bioreactor unit and release the processed fluid to said out-port, wherein said fluid circulates through said bioreactor unit prior to being received by the container; and
   bypass structure having an isolated section, said bypass structure upon actuation isolating said conduit from the plasma separation apparatus so that fluid from the apparatus is allowed to flow through the conduit and fluid from the plasma separation apparatus is allowed to independently flow through the isolated section of the bypass structure.

17. The apparatus of claim 16 further comprising a second in-port and a cell inoculation device for inoculating cells into said bioreactor unit, said inoculation device connected to said in-port and having:

a receptacle with an interior volume and an entrance for receiving cells into said interior volume;

a pressure mechanism, attached to said receptacle, for providing a positive pressure within the interior volume of said receptacle with respect to the external atmosphere of said receptacle to induce the withdrawal of the cells from said receptacle; and a tube extending from an exit of said receptacle configured to allow the withdrawal of the cells from the interior volume.

18. The apparatus of claim 16 wherein said container includes a vent to allow the escape of gas.

19. The apparatus of claim 16 wherein said oxygenator is integrally connected to a heater adapted to maintain the fluid within a temperature range.

20. The apparatus of claim 16 further comprising a filter, connected within said conduit, for filtering the fluid, wherein the fluid from said in-port circulates through said filter prior to being received by said oxygenator and then by said bioreactor unit.

21. The apparatus of claim 16 wherein the bypass structure includes a bridge section connected between the conduit and the isolated section.

* * * * *